United States Patent
Deshpande

(10) Patent No.: US 9,247,765 B2
(45) Date of Patent: Feb. 2, 2016

(54) STABLE BEADLETS OF LIPOPHILIC NUTRIENTS

(75) Inventor: Jayant Deshpande, New Bombay (IN)

(73) Assignee: OmniActive Health Technologies Limited, Mumbai (IN)

( * ) Notice: Subject to any disclaimer, the term of this patent is extended or adjusted under 35 U.S.C. 154(b) by 2215 days.

(21) Appl. No.: 10/901,748

(22) Filed: Jul. 29, 2004

(65) Prior Publication Data

US 2005/0095301 A1    May 5, 2005

(30) Foreign Application Priority Data

Jan. 14, 2004   (IN) .................................. 28/CHE/04

(51) Int. Cl.

| | | |
|---|---|---|
| A23L 1/30 | (2006.01) | |
| A61K 9/64 | (2006.01) | |
| A61K 9/16 | (2006.01) | |
| A61K 9/50 | (2006.01) | |
| A23L 1/303 | (2006.01) | |
| A61K 9/20 | (2006.01) | |
| A61K 36/53 | (2006.01) | |
| A61K 36/82 | (2006.01) | |
| A61K 36/9066 | (2006.01) | |
| A61K 36/9068 | (2006.01) | |
| A23L 1/302 | (2006.01) | |

(52) U.S. Cl.
CPC .............. *A23L 1/3002* (2013.01); *A23L 1/302* (2013.01); *A23L 1/303* (2013.01); *A23L 1/3006* (2013.01); *A61K 9/2081* (2013.01); *A61K 9/5047* (2013.01); *A61K 9/5078* (2013.01); *A61K 36/53* (2013.01); *A61K 36/82* (2013.01); *A61K 36/9066* (2013.01); *A61K 36/9068* (2013.01); *A61K 9/1676* (2013.01)

(58) Field of Classification Search
None
See application file for complete search history.

(56) References Cited

U.S. PATENT DOCUMENTS

| | | | |
|---|---|---|---|
| 3,998,753 A | 12/1976 | Antoshikiw et al. | |
| 4,254,100 A | 3/1981 | Keller et al. | |
| 4,477,492 A * | 10/1984 | Bergna et al. | 427/215 |
| 4,670,247 A | 6/1987 | Scialpi | |
| 4,929,774 A | 5/1990 | Fukamachi et al. | |
| 5,811,609 A | 9/1998 | Vilstrup et al. | |
| 5,849,345 A | 12/1998 | Giger et al. | |
| 5,882,713 A | 3/1999 | Eskins et al. | |
| 6,093,348 A * | 7/2000 | Kowalski et al. | 252/363.5 |
| 6,531,157 B1 | 3/2003 | Hähnlein et al. | |
| 6,582,721 B1 * | 6/2003 | Lang | 424/439 |
| 6,663,900 B2 * | 12/2003 | DeFreitas et al. | 424/492 |
| 2001/0036480 A1* | 11/2001 | Etter | 424/489 |
| 2003/0012815 A1* | 1/2003 | Ishibashi et al. | 424/471 |
| 2003/0064133 A1 | 4/2003 | Blatt et al. | |

FOREIGN PATENT DOCUMENTS

| | | |
|---|---|---|
| EP | 0 229 652 | 7/1987 |
| JP | 5-70793 A | 3/1993 |
| JP | 6-181725 A | 7/1994 |
| JP | 7-67574 A | 3/1995 |
| JP | 2000-350555 A | 12/2000 |
| JP | 2002-104958 A | 4/2002 |
| WO | 97/35487 | 10/1997 |
| WO | 00/27362 | 5/2000 |
| WO | 01/51026 | 7/2001 |
| WO | 2004/080199 | 9/2004 |

OTHER PUBLICATIONS

Notification of Reasons for Refusal issued Jun. 23, 2009 by the Japanese Patent Office in related Application No. JP 2006-500384.
JRS Pharma LP *Non-Pareil Seeds*, Mar. 2003, SdT nach Art. 54(2) (4 pages).
Produktformen—Vitamine und Carotinoide, Hoffmann La Roche, Mar. 2000 (4 pages) translation provided (6 pages).

* cited by examiner

*Primary Examiner* — Mina Haghighatian
*Assistant Examiner* — Luke Karpinski
(74) *Attorney, Agent, or Firm* — Hamre, Schumann, Mueller & Larson, P.C.

(57) ABSTRACT

The invention disclosed in this application relates to novel stable beadlets of lipophilic nutrients comprising an inert core having a coating of stabilizing antioxidants, lipophilic nutrients, or mixtures thereof. The beadlets may be coated with one or more coatings to protect the lipophilic ingredients from the atmosphere, specifically the coatings can be used to protect against moisture and/or oxygen. The invention also relates to a process for the preparation of the stable beadlets. The beadlets can be used in medicines and dietary supplements intended to facilitate the reduced risk of macular degeneration, cataract, and several forms of cancer.

24 Claims, No Drawings

STABLE BEADLETS OF LIPOPHILIC NUTRIENTS

The present invention relates to novel beadlets of lipophilic nutrients and a process for their preparation. The present invention, particularly relates to novel and stable beadlets of lipophilic nutrients, materials, or substances, particularly nutrients like carotenoids, tocopherols, tocotrienols, plant sterols and stanols, and lecithins, select omega-3 fatty acids and poly-unsaturated fatty acids, more particularly novel beadlets of lutein, lutein esters, zeaxanthin, zeaxanthin esters, and a process for their preparation.

BACKGROUND OF THE INVENTION

The role of nutrients and phytochemicals in the promotion of good health through nutrition has now been extended to the likely benefits such as prevention of cancer, and protection against many other chronic diseases like arthritis, coronary heart disease, osteoporosis, and possibly many others.

A number of phytochemical nutrients have a lipophilic characteristic, such as tocopherols, tocotrienols, carotenoids, plant sterols and stanols, and lecithins, select omega-3 fatty acids and polyunsaturated fatty acids. The terms "lipophilic nutrient(s)" or "lipophilic phytochemical(s)" or "active lipophilic nutrient(s)" are interchangeably used for describing these compounds singly or in combination with other such compounds, while describing the current invention. Lipophilic nutrients are a class of substances which exhibit an affinity towards oily or fatty solvents or carriers. Lipophilic substances have a higher solubility in hydrocarbon solvents, such as hexane, and have poor water solubility.

Tocopherols, tocotrienols and carotenoids are naturally occurring lipophilic micronutrients, suggested to play a role in the prevention of several degenerative diseases. Plant sterols or stanols are naturally occurring lipophilic compounds structurally related to cholesterol found in nuts, vegetable oils, seeds, cereals and beans. Lecithins are complex lipophilic mixtures of glyceride oils and phosphatides (including phosphaptidylcholine, or PC) which are widely used in food-processing, and are now being used as dietary supplements for their possible role as a source of choline which is required for cell-membrane integrity and for a wide variety of biochemical and neurochemical processes within the body. Poly-unsaturated fatty acids (such as linolenic acid, alpha-linolenic acid, and gamma-linolenic acid) and omega-3 fatty acids (such as AA, DHA and EPA) have a significant nutritional role to play with several metabolic processes and healthy body function.

Carotenoids and other lipophilic nutrients are useful as nutritional supplements for the prevention/treatment of diseases, such as, several forms of cancer, immunological disorders, eye disorders, skin manifestations, inflammation, cardio-vascular disease etc. These lipophilic nutrients are typically required to be administered daily through a suitable delivery system. There are several delivery systems such as emulsions and suspensions or oily solutions that are popularly used currently along with solid delivery forms such as gelatin beadlets.

Many of these lipophilic phytochemicals and nutrients are sought to be incorporated in formulations of nutritional supplements in a stable, standardized form. While these are typically available in oily, waxy or viscous form, there is often a need to present these in a dry delivery form, which provides standardized quantities of these phytochemicals with adequate protection against destabilizing influences of light, moisture or oxygen, or from contact with other reactive components of a multi-ingredient nutrient supplement or health food.

Issues in Formulating Products With Lipophilic Nutrients:

1. Difficulty in developing dry-delivery form:

Many nutritional formulations in the industry are in the form of tablets, capsules or dry-mixes. It is a major problem for formulators and manufacturers of such supplements to incorporate lipophilic nutrients such as carotenoids, vitamin E sources like tocopherols and tocotrienols, concentrated forms of PC-rich lecithins, phytosterols and plant stanols, various PUFA rich oils and omega-3 fatty acids singly or in combination with other nutrients into dry forms due to the oily, waxy or viscous nature of these products. Some options like spray dried powders, granules or gelatin beadlets work only with select products, and do not necessarily function well under tabletting systems. Some of the challenges in using lipophilic nutrients are explained below:

a. Carotenoids tend to be unstable at room temperature, and prone to degradation on exposure to light, heat, air and acidic environment. Their life needs to be extended by the use of other stabilizing anti-oxidants such as natural tocopherols, ascorbic acid derivatives and citrate.

b. Another option for stabilizing carotenoids is by delivering the same in an oil medium to provide the protective cover of the oils along with naturally present, or added anti-oxidants. Dry delivery forms are considered more difficult to stabilize.

c. Tocopherols and tocotrienols are typically found in an oily medium in the presence of vegetable oils. Such oily products are difficult to use except in the smallest of doses in dry delivery forms such as tablets without the use of specialized technologies to convert them to powders, granules or beadlets.

d. Lecithins rich in the active ingredient PC (20-95%) tend to be viscous pastes or waxy masses which are not suitable for directly compressible or free-flowing powders.

e. Phytosterols and plant stanols are oily products that have typically been supplemented through fat based supplements. Incorporating these into free flowing or directly compressible dry delivery forms would significantly increase the number of options for formulators and manufacturers of nutritional supplements.

f. PUFAs, GLA and Omega-3 Fatty Acids are currently used sparingly and infrequently in tablet and capsule based supplements due to their oily nature. Conventional dry delivery conversion technologies do not provide good solutions for free flowing, directly compressible beadlets.

2. Difficulties in Stabilizing Lipophilic Nutrients:

By nature, carotenoids are unstable at room temperature. Their stability is affected by light, heat, air (oxygen) and acidic environment. It is known that their stability can be enhanced by the addition of certain stabilizing antioxidants such as natural tocopherols, ascorbic acid derivatives and citrate.

Carotenoids and other lipophilic nutrients are typically used as ingredients for nutritional supplement formulations either as dispersions in oil or as powders, granules or beadlets for making tablets or filling in capsules. In the form of oil dispersion, these nutrients are generally encapsulated in soft gelatin capsules. Some of these, such as carotenoids are also manufactured as cold water dispersible powder for use in fruit juices and other aqueous beverages. Out of these three forms, beadlets have the advantage of being suitable for further formulation into compressed tablets or encapsulated in hard gelatin capsules.

At present beadlets of carotenoids and other lipophilic nutrients are typically manufactured by spray drying a mixture of said active nutrients and gelatin along with sucrose, and stabilizers. In such beadlets the carotenoid/lipid particles are protected from light and oxygen in the matrix of gelatin and sucrose formed during the spray drying process in which matrix the carotenoid/lipoid particles are embedded. The spray-dried product is made less cohesive by covering with starch.

Processes for the preparation of beadlets have been described in numerous references. Dry formulations of fat soluble vitamins have been disclosed. Hahnlein et al. (U.S. Pat. No. 6,531,157). Starch-based emulsions have also been proposed as a mechanism for incorporating water-immiscible substances into a homogenous composition. Eskins et al. (U.S. Pat. No. 5,882,713). See also, e.g., U.S. Pat. No. 3,998,753; U.S. patent Application No. 2003/0064133, U.S. Pat. Nos. 4,254,100, 4,670,247, 4,929,774, 5,811,609, 6,093,348, 6,582,721, 5,849,345, and 6,663,900. Despite these methods, there remains a desire for a better way to formulate lipophilic substances into a stable, useable form. The beadlets obtained by the above known processes do not ensure stability to the active material either in the beadlet form itself, or when formulated into tablets. In addition, none of the hitherto known methods of making beadlets provide desirable physical characteristics, such as spherical, free flowing beadlets suitable for tabletting or capsule filling. Further, the beadlets produced by hitherto known methods do not prevent leaching of the active nutrients contained in such beadlets when subjected to compression to form tablets.

Most of these processes employ gelatin, a protein isolated from the bones and muscles of the animals. In recent times, use of excipients of animal origin in herb-based nutraceuticals is considered undesirable by a large section of users. Due to poor digestibility, use of gelatin based formulations have a limitation for use among the geriatric population. Sometimes, lactose is used as an excipient in the main beadlet matrix due to its compressible nature, but its dairy product (animal) origin makes it unacceptable to many, and is therefore considered to be undesirable.

At present, the nutraceutical industry needs:
a. a solid form of active ingredients (carotenoid and lipids), such as beadlets, suitable for formulation into tablet,
b. beadlets from which the active ingredients do not leach out when compressed into tablets,
c. beadlets which can be protected from light or oxygen or moisture,
d. beadlets preferably free from excipients of animal origin (including dairy products),
e. beadlets which can be produced conveniently using a simple process and equipment that are common,
f. beadlets which have an appealing, uniformly spherical appearance.

Thus, the formulation of oral delivery systems for lipophilic nutrients, particularly carotenoids such as lutein, lycopene, beta carotene, present a challenge to the pharmaceutical and food industries, due to the oily nature and instability of the carotenoids/lipids.

By nature, carotenoids and lipophilic nutrients are unstable in presence of oxygen and light. Therefore, they can be stabilised by the incorporation of certain stabilising antioxidants. To further enhance stability, the active nutrients (e.g. carotenoids, or lipophilic nutrients such as tocopherols or tocotrienols etc) can be coated with polymer(s) that provide protection against the harmful effects of oxygen, light and moisture.

Non-pareil seeds such as sugar spheres or globules, without the active ingredient, on which the active ingredient is coated, are a convenient form for the preparation of oral dosage forms such as tablets or hard gelatin capsule, of the active ingredient. The beadlets produced by coating the active ingredient on the non-pareil seeds are uniformly spherical in nature and can be used in a size as small as about 250 microns. The active ingredient—loaded beadlets, having a generally spherical shape, may further be uniformly coated with a polymeric material to modify the release or mask the bitter taste of the drug.

In fluidisation process, the medium of coating can either be aqueous or organic. Attempts have been made in the past to apply fluid bed technology for preparing microcapsules of carotenoids using aqueous coating process on crystalline sucrose. Such processes suffer from drawbacks such as use of high temperature (180.deg. F), which are not suitable for many heat sensitive products such as carotenoids.

Unfortunately, this method using organic solvent medium is not applicable directly for the formation of beadlets of lipophilic nutrients, such as carotenoids, in spite of the above said advantages, due to their oily/waxy nature. Further these nutrients, when subjected to fluidization, form a cohesive mass, which adversely affects the fluidization. Therefore a process employing fluid-bed system using a non-aqueous coating medium has hitherto not been considered possible or demonstrated, for the preparation of beadlets of lipophilic nutrients such as carotenoids.

SUMMARY OF THE INVENTION

The present invention involves the coating of an inert core with lipophilic nutrients and/or stabilising antioxidants. The lipophilic nutrients and/or stabilising antioxidants can be supplied in an organic solvent medium and applied to the inert core by fluidisation technique. The resulting beadlets can be successfully employed in pharmaceutical and food industries.

According to the present invention, a process of coating an inert core with lipophilic materials or nutrients, particularly carotenoids, employing a fluidised bed technique in an organic solvent medium is possible. This was possible when we found that a solution of lipophilic nutrients, in a non-polar solvent when diluted with a polar solvent forms a colloidal suspension. This colloidal suspension when subjected to fluidisation using a fluid bed system employing an inert core did not form a cohesive mass and does not adversely affect the fluidisation process. On the contrary, the process resulted in the formation of inert cores uniformly coated with the lipophilic materials or nutrients in the form of uniformly spherical beadlets.

In other words, the fluidisation technique using a non-aqueous solvent which hitherto was not considered as applicable for the formation of beadlets of lipophilic nutrients, has been made possible by the process developed according to the present invention. This invention has resulted in developing a new concept enabling incorporation of oily lipophilic matter into beadlets.

The formation of stable, uniformly coated free flowing spherical beadlets of lipophilic nutrients is a result of the combination of the use of spherical inert cores (nonpareil seeds) and selected stabilising antioxidants and coating the resulting combination with oxygen and moisture barrier polymers to provide additional protection.

The stability of the beadlets of lipophilic nutrients achieved by this invention depends upon the judicious selection of the protective agents and coatings, and process conditions described in this invention. With the use of appropriate packing of the beadlets, such as sealed containers, by which exposure of the beadlets to moisture or air can be diminished or even eliminated, with commercially acceptable storage temperatures ranging from about 10 to about 30 degrees C., shelf life and stability of the actives for periods ranging from 6 months to 36 months, or higher as may be required- and tested as per ICH guidelines for the same-are possible.

The spherical nature of the beadlets has several advantages such as, free flowing property which is required during tablet compression, enables compression of tablets using a compression force as high as 10 kg/cm$^2$, superior release property, possibility of site specific controlled release of carotenoids and lipids, and consequently, higher bioavailability. The major advantage of using such technology is that it avoids the use of high temperature (above 50 degree C.) during preparation of beadlets and thus prevents degradation of heat-sensitive bioactive compounds. Another advantage of using spherical cores is the broader range of beadlet size which can range between about 250 microns to about 3.50 mm. The beadlet size can also be from about 250 microns to about 2.0 mm. Another advantage of the present invention is that the invention can be practiced using existing fluid-bed technology and equipment.

DETAILED DESCRIPTION OF THE PREFERRED EMBODIMENT

Accordingly, the present invention provides novel stable beadlets of lipophilic nutrients, which comprise an inert core having a coating of a mixture of stabilizing antioxidants and a lipophilic nutrient or mixtures thereof.

The novel beadlets of the present invention are obtained by coating one lipophilic nutrient, or a mixture of such nutrients on a central inert core to obtain uniform, generally spherical beadlets. The uniform, generally spherical, appearance of these beadlet provides excellent free flowing characteristics, which are very desirable for manufacturing and formulating operations. These novel beadlets are convenient to use, and have a stronger visual appeal. The novel beadlets of the present invention also may be stabilized synergistically with the use of anti-oxidants and with the application of layers of polymeric materials as coatings, preferably gelatin free, on the beadlets as barriers to prevent penetration of light, moisture and/or air. The beadlets of the present invention are well suited for use as directly compressible ingredients in tablets, or in two-piece capsules.

In one embodiment of the present invention the inert core may be comprised of any material that does not react with the lipophilic nutrient or carotenoid employed for coating. It can be selected from non-pareil seeds made of carbohydrates such as sugar, mannitol, starch, sago, or microcrystalline cellulose. More preferably, the core used may be seeds such as sugar spheres, mannitol spheres, or the like. The inert core can generally be in the form of a sphere, and can have a diameter from about 200 microns to about 3 mm and still yield a stable beadlet. The inert core can also have a diameter of about 200 microns to about 1.5 mm.

One embodiment of the current invention includes lipophilic nutrients in the coating. Lipophilic nutrients refers to a class of compounds that show an affinity towards oily or fatty solvents or carriers, such as hexane, or otherwise have a higher solubility in hydrocarbons than water, and may be used in the current invention. The beadlets can comprise from about 1 wt. % to about 50 wt. % lipophilic nutrient.

In one embodiment of the present invention the lipophilic nutrients used in the coating are carotenoids, tocopherols, tocotrienols, plant sterols and stanols, and lecithins, select omega-3 fatty acids, and poly-unsaturated fatty acids, or mixtures thereof. The lipophilic nutrients may comprise carotenoids such as lutein, lutein esters, zeaxanthin, alpha-carotene, beta-carotene, natural lutein or zeaxanthin esters, astaxanthin, or lycopene. The beadlets can contain a mixture of these substances as well. For instance, the stable beadlets can comprise xanthophyll esters containing lutein and zeaxanthin fatty acid esters in which about 90 wt. % to about 95 wt. % is trans-lutein esters, 0 wt. % to about 5 wt. % is cis-lutein esters and about 3.5 wt. % to about 6 wt. % is zeaxanthin esters. The beadlets can also comprise xanthophyll crystals that comprise at least about 85 wt. % total xanthophylls in which at least about 90 wt. % is trans-lutein and/or zeaxanthin.

The beadlets may also contain lipophilic nutrients such as vitamin A, vitamin D, or vitamin E in the form of mixed tocopherols or tocotrienols; vitamin K, medium chain triglycerides, and the like, or a mixture of such lipophilic nutrients. The lipophilic nutrients may also comprise lecithins such as mixtures of glyceride oils and phosphatides (including phosphaptidylcholine); plant stanols and/or sterols; poly-unsaturated fatty acids such as linolenic acid, alpha-linolenic acid, and gamma-linoleic acid; omega-3 fatty acids such as AA, DHA and EPA; tocopherols such as $\alpha$, $\beta$, $\chi$, and $\gamma$ tocopherols; tocotrienols such as $\alpha$, $\beta$, $\chi$, and $\gamma$ tocotrienols; vegetable oils such as soya oil, partially or fully hydrogenated soya oil, cotton oil, coconut oil, palm-kernel oil, maize oil, palm oil, sunflower oil, olive oil, sesame oil, linseed oil, hazelnut oil, walnut oils, safflower oil, corn oil, peanut oil, vegetable oils having an unsaturated long chain fatty acid content of about 30 wt. % to about 90 wt. %, or any blends or fractions of these vegetable oils. The lipophilic nutrient can also be lipophilic substances that have diuretic and cosmetic application such as the oils of avocado, pear, blackcurrant, borage, castor, evening primrose, wheat-germ, and the like. Of course, the lipophilic nutrients can comprise combinations of the above ingredients. For instance, various lipophilic nutrients could be diluted using one or more of the above vegetable oils. One having ordinary skill in the art would understand that this list of potential lipophilic substances is not exhaustive, and there are many other lipophilic nutrients that offer medicinal, nutritional, pharmaceutical, or some other health or cosmetic benefit, which may also be utilized in the current invention.

In a preferred embodiment, the novel beadlets of the present invention may be in the form of spheres, globules and the like. The size of the beadlets of the present invention may range between about 250 microns to about 3.5 mm, more preferably about 250 microns to about 2.0 mm. By the term spherical, the inventors intend to describe the free flowing nature of the beadlets, and do not intend to mean a geometrically spherical beadlet. The generally spherical shape of the beadlets provides for a substantially free-flowing embodiment. The free-flowing capability of the beadlets can be determined by measuring the angle of repose. The angle of repose is determined by allowing the beadlets to drop from a funnel held at a certain height and form a conical heap on a level, flat surface. The angle of repose is the angle of the beadlet heap relative to the horizontal, flat plane. The beadlets of the invention have an angle of repose preferably between about 20 to about 30 degrees, more preferably about 22 to about 27 degrees, and most preferably between about 23 to about 25 degrees.

In another preferred embodiment of the present invention the novel beadlets may have a coating of a film of oxygen barrier polymer.

In another preferred embodiment of the present invention the novel beadlets may also have another coating, over the oxygen barrier polymer, with a film of a moisture barrier polymer. One with skill in the art will recognize that one coating may be used to provide both of these attributes.

In a preferred embodiment, the coatings are gelatin-free, and include only naturally derived materials. Such naturally derived materials can comprise components which can be derived or isolated from vegetables.

The polymer used for coating for providing protection to the lipophilic nutrient matrix against oxygen may be selected from hydroxy propyl cellulose, hydroxy propyl methyl cellulose, methacrylate copolymers, polyvinyl pyrrolidone, ethyl cellulose, carboxymethyl cellulose, polyvinyl alcohol, and the like, or their mixtures. Their amount may range from about 1 to about 40% of the weight of beadlets.

The polymer which can be used for providing a barrier to the entry of moisture can be selected from carboxy methyl cellulose sodium, hydroxy propyl cellulose, hydroxy propyl methyl cellulose, methacrylate copolymers, polyvinyl alcohol and the like. If present, the moisture barrier polymer can account for about 1% to about 40% of the weight of beadlets. The beadlets can also comprise about 2 wt. % to about 20 wt. % moisture barrier polymer. It should be understood that a single polymeric coating may act as both a moisture and oxygen barrier. Of course, two different coatings can be used to act as an oxygen barrier and as a moisture barrier, respectively.

The lipophilic nutrients can also be provided with stabilising antioxidants. Some stabilising antioxidants which may be employed to form the mixture of the lipophilic nutrients include vitamin E acetate, natural tocopherols, ascorbyl palmitate, ascorbic acid, sodium ascorbate, citric acid, rosemary extract or rosemary oil, curcuminoids, green tea extract, ginger extract, camosic acid, butylated hydroxy anisole, butylated hydroxy toluene and the like or their combinations thereof. When present, their amount used may vary from about 0.1% to about 20% by weight of the carotenoid, lipophilic nutrient, or lipid used. To ensure an even distribution in the beadlet, the lipophilic nutrient may be mixed with a stabilizing antioxidant prior to coating of the inert core.

The beadlets can contain other stabilisers, such as sorbic acid, sodium benzoate, sodium salicylate, EDTA, and the like or mixture thereof.

In another embodiment of the present invention there is provided a process for the preparation of the novel beadlets of lipophilic nutrients as defined above which comprises.
 (i) forming a colloidal suspension of the desired lipophilic nutrients by dissolving the same in a non-polar solvent and diluting the resulting solution with a polar solvent.
 (ii) mixing the colloidal suspension obtained with a stabilising antioxidant,
 (iii) spraying the resulting colloidal suspension on to inert cores present in a fluid-bed system provided with a bottom spray mechanism, at a temperature in the range of ambient temperature to 45 degree C., at an atomisation pressure in the range of about 0.5 to about 3 Kg/cm$^2$ and a spray rate in the range of about 10 g/hour to about 600 g/hour, and
 (iv) drying the beadlets formed at an atomisation pressure of about 0.8 kg/cm$^2$ to about 1.2 kg/cm$^2$.

In still another embodiment of the present invention there is provided a process for the preparation of the beadlets of lutein or any other carotenoid, which comprises:
 (i) forming a colloidal suspension of desired carotenoid by dissolving the carotenoid in a non polar solvent and diluting the resulting solution with a polar solvent,
 (ii) mixing the colloidal suspension obtained with a stabilising antioxidant,
 (iii) spraying the resulting colloidal suspension on to inert cores present in a fluid-bed system provided with a bottom-spray mechanism at a temperature in the range of ambient temperature to about 45 degree C., at an atomisation pressure in the range of about 0.1 kg/cm$^2$ to about 3 kg/cm$^2$ and a spray rate in the range of about 10 g/hour to about 600 g/hour, and
 (iv) drying the resulting beadlets at an atomisation pressure of about 0.8 Kg/cm$^2$ to about 1.2 Kg/cm$^2$.

Various parameters of this process can be modified. For instance, the colloidal suspension can be sprayed at a bed temperature from about 25 degree C. to about 40 degree C., or even from ambient temperature to about 32 degree C. In addition, the atomization pressure during spraying can be from about 0.5 kg/cm$^2$ to about 3 kg/cm$^2$, or even from about 1.0 kg/cm$^2$ to about 2.5 kg/cm$^2$.

In a preferred embodiment the non-polar solvents which may be used for preparing the colloidal suspension of the lipophilic nutrient include methylene chloride, chloroform, petroleum ether (low boiling), petroleum ether (high boiling) or mixtures thereof.

In another preferred embodiment, the polar solvents, which may be used for preparing the colloidal suspension of the lipophilic nutrient include isopropyl alcohol, acetone, methanol, ethanol, acetonitrile or mixtures thereof.

The non-polar solvent and polar solvent can be used in varying ratios. For instance, the non-polar and polar solvents can comprise a mixture of methylene chloride and isopropyl alcohol at a ratio of about 1:1 to about 0.1:1. The non-polar and polar solvents can also comprise a mixture of methylene chloride and isopropyl alcohol at a ratio of about 0.2:1 to about 2:1.

The lipophilic nutrients can be mixed with polar solvent directly. It may be noted that carotenoids or lipophilic nutrients are not completely soluble in polar solvent. This means that only some part of the carotenoid or lipophilic nutrient may form a suspension. This suspension may not be homogeneous due to the presence of large particles of the undispersed carotenoids or lipophilic nutrients. This suspension can be filtered to remove the solid materials and the resulting colloidal suspension can be used for the fluidisation process.

Although such a process is possible and envisaged within the broad scope of the present invention, the process is not economical and efficient. When carotenoids are mixed with polar solvent directly, some portion of the carotenoid forms colloidal suspension, where as a large portion remains as a lumpy, un-dispersed solid mass. One can filter such a mixture and use only the colloidal dispersion portion for coating. If one follows this procedure, it is not always possible to load an adequate quantity of carotenoid, and therefore not economical. Therefore it is desirable to first dissolve or disperse the carotenoid in non-polar solvent, and thereafter form a colloidal dispersion by the addition of polar solvent.

The stabilising antioxidants used may include vitamin E acetate, natural tocopherols, ascorbyl palmitate, ascorbic acid, sodium ascorbate, citric acid, rosemary extract or rosemary oil, curcuminoids, green tea extract, ginger extract, carnosic acid, butylated hydroxy anisole, butylated hydroxy toluene and the like or combinations thereof. When the stabilising antioxidants are used, the amount used may vary from about 0.1% to about 20% by weight of the carotenoid, lipophilic nutrient or lipid used. The stabilising oxidants may also contain other stabilisers which may include sorbic acid, sodium benzoate, sodium salicylate, EDTA, and the like or mixtures thereof.

Binding agents may be added along with the stabilising antioxidants for enhancing the efficiency of the coating. If used, the binding agents used may include gum acacia, gum tragacanth, xanthan gum, polyvinyl pyrrolidone, hydroxypropyl cellulose, hydroxypropyl methyl cellulose (5 cps), hydroxypropyl methyl cellulose (15 cps), cellulose or their mixtures. Their amount used may range from about 0.1% to about 10% of the weight of the beadlets. It may be advantageous to mix the binding agent with the colloidal suspension prior to spraying the suspension in the fluid-bed system.

Disintegrating agents may also be used along with the binding agents. If such agents are used they may be selected from starch, cross-linked polyvinyl pyrrolidone, cross-carmelose sodium and sodium starch glycolate or mixtures thereof. Their amount used may range from about 0.1% to about 5% of the weight of the beadlets. Disintegrating agents can also be combined with stabiliser. For instance, the beadlets can comprise from about 0.1 wt. % to about 20 wt. % stabiliser and/or disintegrating agent. Of course, the beadlets can contain stabiliser, binding agent, and disintegrating agent.

In another preferred embodiment of the present invention, the novel beadlets are provided with a coating of a layer of films of an oxygen barrier polymer.

In yet another preferred embodiment of the present invention, the novel beadlets are provided with another coating over the layer of the coating of films of an oxygen barrier polymer, with a film of a moisture barrier polymer.

The details of the invention are provided in the examples given below which are given for illustrative purposes only and therefore should not be construed to limit the scope of the invention which is defined by the claims.

EXAMPLES

Example 1

Preparation of Beadlets Containing Lutein From Petals of Marigold Flower

Step 1 Preparation of Xanthophyll Crystals

The preparation of xanthophyll esters concentrate is described in Indian Patent Application No. 622/Mas/2002, U.S. Pat. No. 6,737,535, and PCT/In 02/00219, the disclosures of which are incorporated by reference herein, and is summarized as follows.

Commercial grade marigold oleoresin (57.98 g) containing 11.54% xanthophyll content (by spectrophotometric method) was mixed with potassium isopropyl alcoholate (prepared by dissolving 15 g potassium hydroxide in 175 ml isopropanol.) The saponification mixture was heated and maintained at 70 degree C. for a period of 3 hours. The degree of hydrolysis was monitored by HPLC during the saponification stage. Isopropanol was distilled off under reduced pressure and the solids obtained were stirred with 230 ml of water at room temperature. The mixture was taken into a separatory funnel and extracted with equal volume of ethyl acetate (3 times). Ethyl acetate layer was collected and washed with distilled water for removing the excess alkali, soapy materials and other water-soluble impurities. The ethyl acetate layer was distilled off under reduced pressure to get saponified crude extract (25.01 g).

This resultant crude extract (25.01 g) was subjected to purification by stirring with 100 ml of hexane/acetone mixture (80:20) at room temperature for 30 minutes, followed by filtration. The precipitate of xanthophyll crystals obtained was washed with methanol. The resulting orange crystals were vacuum dried at ambient temperature for 72 hrs.

The yield of the xanthophyll crystals was 3.41% (1.98 g). Xanthophyll content was 86.23% by weight (as determined by UV/Vis spectrophotometry) out of which the contents of trans-lutein, zeaxanthin, and other carotenoids were 91.43%, 6.40% and 2.17% respectively as determined by HPLC analysis.

Step 2-Conversion of Above Xanthophyll Crystals to Beadlets

Carotenoids in the form of Xanthophyll crystals as described in step 1 a above (92 g, containing 86.23% Xanthophylls by weight (78.84% trans-lutein) were suspended in a mixture of 300 g isopropyl alcohol and 800 g methylene chloride. A solution of 10 gm of Hydroxypropylmethyl cellulose (5 cps) in 200 g isopropyl alcohol and 100 g methylene chloride was added to the above suspension along with 20 g natural tocopherol, 40 g ascorbyl palmitate and 15 g sodium starch glycolate. The suspension was strained through 100 mesh filter.

300 g of non-pareil seeds made of sugar, were charged into a Uni-Glatt fluid bed processor with bottom spray, and warmed for 30 minutes at 35 degree C. The carotenoids suspension as prepared above was sprayed on the non-pareil seeds at the rate of 500 g/hour. The bed temperature was maintained at 35 degree C. Atomization pressure of 1.2 kg/cm$^2$ was maintained. 470 g of carotenoid loaded beadlets showing 9.46% trans-lutein were obtained.

80 g of polymer mixture comprising 32 g of ethyl cellulose and 48 g of hydroxypropyl methyl cellulose was dissolved in solvent mixture comprising 500 g of methylene chloride and 1000 g of isopropanol. 8 g of polyethylene glycol 600 was added as plasticiser. With this solution the coating was performed on carotenoid loaded non-pareil seeds in UniGlatt fluid bed coater using bottom spray technology at a spray rate of 400 g per hour. An atomization speed of 1.2 kg/cm$^2$ was maintained. Bed temperature of 38 degree C. was maintained through out the coating process. 540 g of oxygen-barrier coated beadlets showing 8.51% trans-lutein content were obtained.

55 g of polyvinyl alcohol was dissolved in 300 g water, mixed with 6 g of polyethylene glycol 400 and 2 g of titanium dioxide and the mixture was sprayed on oxygen-barrier coated non-pareil seeds using Uni-Glatt fluid-bed coater using bottom spray mechanism. A bed temperature of 45 degree C. was maintained during coating. Atomisation pressure of 1.5 kg/cm$^2$ was maintained. A spray rate of 150 g/hour was used. 580 g of moisture barrier coated carotenoid beadlets showing 6.8% trans-lutein content were obtained.

Example 2

Preparation of beadlets containing Free Lutein in Oil Suspension from petals of Marigold Flower Lutemax® Free Lutein Oil Suspension (obtained from Marigold flower petals) (110 g free lutein oil suspension in 220 g safflower oil) was suspended in a mixture of 150 g isopropyl alcohol and 800 g chloroform. A solution of 5 gm of hydroxypropylmethyl cellulose (15 cps) in 200 g isopropyl alcohol and 100 g methylene chloride was added to the above suspension along with 20 g natural tocopherol, 40 g ascorbyl palmitate and 15 g sodium starch glycolate. The suspension was strained through 100 mesh filter.

250 g of non-pareil seeds made of sugar, were charged into a Uni-Glatt fluid bed processor with bottom-spray, and warmed for 30 minutes at 35 degree C. The carotenoid suspension as prepared above was sprayed on the non-pareil seeds at the rate of 500 g/hour. The bed temperature was maintained at 35 degree C. Atomisation pressure of 1.2 kg/cm$^2$ was maintained. 510 g of carotenoid loaded beadlets showing 8.1% trans-lutein were obtained.

80 g of polymer mixture comprising 10 g of ethyl cellulose and 70 g of hydroxypropyl methyl cellulose was dissolved in solvent mixture comprising 500 g of methylene chloride and 1000 g of isopropyl alcohol, 8 g of polyethylene glycol 600 was added as plasticiser. With this solution the coating was performed on carotenoid loaded non-pareil seeds in Uni-Glatt fluid bed coater using bottom spray technology at a spray rate of 400 g per hour. An atomization speed of 1.2 kg/cm$^2$ was maintained. Bed temperature of 38 degree C. was maintained through out the coating process. 580 g of oxygen-barrier coated beadlets showing 7.2% trans-lutein content were obtained.

60 g of sodium carboxymethyl cellulose dissolved in 300 g water, then mixed with 6 g of Polyethylene glycol 400 and 2 g of titanium dioxide was sprayed on oxygen-barrier coated non-pareil seeds using Uni-Glatt fluid-bed coater using bottom spray mechanism. A bed temperature of 45 degrees C. was maintained during coating. Atomisation pressure of 1.5 kg/cm2 was maintained. A spray rate of 150 g/hour was used. 610 g of moisture barrier coated carotenoid beadlets showing 6.5% trans-lutein content were obtained.

Example 3

Preparation of Beadlets Containing Lutein from Petals of Marigold Flower

Lutemax® Free Lutein (92 g, containing 78.84% trans-lutein) was suspended in a mixture of 100 g isopropyl alcohol and 900 g methylene chloride. A solution of 80 gm of polyvinyl pyrrolidone in 400 g isopropyl alcohol and 100 g methylene chloride was added to the above suspension along with 20 g natural tocopherol, 40 g ascorbyl palmitate and 15 g sodium starch glycolate. The suspension was strained through 100 mesh filter.

300 g of non-pareil seeds made of sugar, were charged in to a Uni-Glatt fluid bed processor with bottom spray, and warmed for 30 minutes at 35 degree C. The carotenoid suspension as prepared above was sprayed on the non-pareil seeds at the rate of 500 g/hour. The bed temperature was maintained at 35 degree C. Atomisation pressure of 1.2 kg/cm$^2$ was maintained. 550 g of carotenoid loaded beadlets showing 9% trans-lutein were obtained.

80 g of polymer mixture comprising 32 g of ethyl cellulose and 48 g of hydroxypropyl methyl cellulose was dissolved in solvent mixture comprising 500 g of methylene chloride and 1000 g of isopropanol. 8 g of polyethylene glycol 600 was added as plasticiser. With this solution the coating was performed on carotenoid loaded non-pareil seeds in Uni-Glatt fluid bed coater using bottom spray technology at a spray rate of 400 g per hour. An atomization speed of 1.2 kg/cm$^2$ was maintained. Bed temperature of 38 degree C. was maintained through out the coating process. 600 g of oxygen-barrier coated beadlets showing 7.9% trans-lutein content were obtained.

60 g of sodium carboxymethyl cellulose dissolved in 300 g water, then mixed with 6 g of Polyethylene glycol 400 and 2 g of titanium dioxide was sprayed on oxygen-barrier coated non-pareil seeds using Uni-Glatt fluid-bed coater using bottom spray mechanism. A bed temperature of 45 degree C. was maintained during coating. Atomisation pressure of 1.5 kg/cm$^2$ was maintained. A spray rate of 150 g/hour was used. 650 g of moisture barrier coated carotenoid beadlets showing 6.6% trans-lutein content were obtained.

Example 4

Preparation of Beadlets Containing 25% Trans-Lutein from Petals of Marigold Flower Marigold extract (382 g, containing 75% trans-lutein) was suspended in a mixture of 1200 g isopropyl alcohol and 2800 g methylene chloride. A solution of 90 gm of hydroxypropylmethyl cellulose (5 cps) in 500 g isopropyl alcohol and 200 g methylene chloride was added to the above suspension along with 60 g natural tocopherol, 80 g ascorbyl palmitate and 15 g cross-carmellose. The suspension was strained through 100 mesh filter.

300 g of non-pareil seeds made of sugar, were charged in to a Uni-Glatt fluid bed processor with bottom spray, and warmed for 30 minutes at 35 degree C. The carotenoid suspension as prepared above was sprayed on the non-pareil seeds at the rate of 500 g/hour. The bed temperature was maintained at 35 degree C. Atomisation pressure of 2 kg/cm$^2$ was maintained. 910 g of carotenoid loaded beadlets showing 29% trans-lutein were obtained.

75 g of polymer mixture comprising 32 g of ethyl cellulose and 48 g of hydroxypropyl methyl cellulose was dissolved in solvent mixture comprising 500 g of methylene chloride and 1000 g of methanol. 8 g of polyethylene glycol 600 was added as plasticiser. With this solution the coating was performed on carotenoid loaded non-pareil seeds in Uni-Glatt fluid bed coater using bottom spray technology at a spray rate of 400 g per hour. An atomization speed of 2.2 kg/cm$^2$ was maintained. Bed temperature of 38 degree C. was maintained through out the coating process. 985 g of oxygen-barrier coated beadlets showing 27.1% trans-lutein content were obtained.

65 g of polyvinyl alcohol dissolved in 300 g water, then mixed with 6 g of Polyethylene glycol 400 and 2 g of titanium dioxide was sprayed on oxygen-barrier coated non-pareil seeds using Uni-Glatt fluid-bed coater using bottom spray mechanism. A bed temperature of 45 degree C. was maintained during coating. Atomisation pressure of 2.5 kg/cm$^2$ was maintained. A spray rate of 150 g/hour was used. 1040 g of moisture barrier coated carotenoid beadlets showing 25.7% trans-lutein content were obtained.

Example 5

Step 1

Preparation Of Xanthophyll Esters Concentrate

The preparation of xanthophyll esters concentrate is described in Indian Patent Application No. 420/Mas/2002, U.S. Pat. No. 6,737,535, and PCT/In 02/00218, the disclosures of which are incorporated by reference herein, and is summarized as follows.

A weighed quantity of marigold oleoresin (150.3 g) with xanthophyll ester content 23.10% and trans-lutein, cis-lutein and zeaxanthin area percentage by HPLC 67.23, 22.08 and 5.18 respectively was transferred into an Erlenmeyer flask (1000 ml) followed by the addition of 750 ml of 2-propanone. This was stirred using a thermostatically controlled stirrer at 15 degree C. to 25 degree C. for a period of 5-10 hours. After an interval of every 2 hours sample was drawn, filtered and the dried precipitated material was analyzed for the ester content and trans-: cis-ratio by HPLC. Finally when the desired degree of the purity had been achieved the solution containing precipitate was filtered through a Buchner funnel and the precipitate was dried in vacuum drier at ambient temperature.

The yield of the resulting concentrate was 20.10 g (13.37%) and the analysis showed xanthophyll ester content 59.26% assayed by spectrophotometric method, measuring at 474 nm. This xanthophyll esters concentrate contained area percentage by HPLC, trans-lutein 92.71, cis-lutein 1.40 and zeaxanthin 5.11 respectively. On visual examination, this concentrate showed an improved orange red color as compared to the starting material, which is dark brown in color.

Step 2. Preparation of Beadlets Containing Xanthophyll Esters and Trans-Lutein Esters from Petals of Marigold Flower Xanthophyll esters concentrate (160 g, containing 59.26% xanthophylls esters by weight-yielding 27.47% trans-lutein on hydrolysis) was suspended in a mixture of 700 g isopropyl alcohol and 600 g methylene chloride. A solution of 80 gm of hydroxypropylmethyl cellulose (15 cps) in 400 g isopropyl alcohol and 100 g methylene chloride was added to the above suspension along with 20 g natural tocopherol, 40 g ascorbyl palmitate and 20 g sodium starch glycolate. The suspension was strained through 100 mesh filter.

320 g of non-pareil seeds made of sugar, were charged in to a Uni-Glatt fluid bed processor with bottom spray, and warmed for 30 minutes at 35 degree C. The carotenoid suspension as prepared above was sprayed on the non-pareil seeds at the rate of 500 g/hour. The bed temperature was maintained at 35 degree C. Atomisation pressure of 1.2 kg/cm$^2$ was maintained. 600 g of carotenoid loaded beadlets showing 10.1% trans-lutein were obtained.

80 g of polymer mixture comprising 10 g of ethyl cellulose and 70 g of hydroxypropyl methyl cellulose was dissolved in solvent mixture comprising 500 g of methylene chloride and 1000 g of isopropanol. 8 g of polyethylene glycol 600 was added as plasticiser. With this solution the coating was performed on carotenoid loaded non-pareil seeds in Uni-Glatt fluid bed coater using bottom spray technology at a spray rate of 400 g per hour. An atomization speed of 1.2 kg/cm$^2$ was maintained. Bed temperature of 38 degree C. was maintained through out the coating process. 680 g of oxygen-barrier coated beadlets showing 8.67% trans-lutein content were obtained.

150 g of polyvinyl alcohol dissolved in 300 g water, then mixed with 6 g of polyethylene glycol 400 and 2 g of titanium dioxide was sprayed on oxygen-barrier coated non-pareil seeds using Uni-Glatt fluid-bed coater using bottom spray mechanism. A bed temperature of 45 degree C. was maintained during coating. Atomisation pressure of 1.5 kg/cm$^2$ was maintained. A spray rate of 150 g/hour was used. 810 g of moisture barrier coated carotenoid beadlets showing 6.0% trans-lutein content were obtained.

Example 6

Preparation of Beadlets Containing Beta-Carotene

Beta-carotene (20% dispersion in palm oil) 160 g, was suspended in a mixture of 900 g isopropyl alcohol and 800 g chloroform. A solution of 80 gm of polyvinyl pyrrolidone in 400 g isopropyl alcohol and 100 g methylene chloride was added to the above suspension along with 20 g natural tocopherol, 40 g ascorbyl palmitate and 12 g. starch. The suspension was strained through 100 mesh filter.

450 g of non-pareil seeds made of sugar, were charged in to a Uni-Glatt fluid bed processor with bottom spray, and warmed for 30 minutes at 35 degree C. The carotenoid suspension as prepared above was sprayed on the non-pareil seeds at the rate of 500 g/hour. The bed temperature was maintained at 35 degree C. Atomisation pressure of 1.2 kg/cm$^2$ was maintained. 650 g of carotenoid loaded beadlets were obtained.

74 g of polymer mixture comprising 10 g of ethyl cellulose and 70 g of hydroxypropyl methyl cellulose was dissolved in solvent mixture comprising 500 g of methylene chloride and 1000 g of methanol. 8 g of polyethylene glycol 600 was added as plasticiser. With this solution the coating was performed on carotenoid loaded non-pareil seeds in Uni-Glatt fluid bed coater using bottom spray technology at a spray rate of 400 g per hour. An atomization speed of 1.2 kg/cm$^2$ was maintained. Bed temperature of 38 degree C. was maintained through out the coating process. 680 g of oxygen-barrier coated beadlets were obtained.

145 g of sodium carboxymethyl cellulose dissolved in 300 g water, then mixed with 6 g of polyethylene glycol 400 and 2 g of titanium dioxide was sprayed on oxygen-barrier coated non-pareil seeds using Uni-Glatt fluid-bed coater using bottom spray mechanism. A bed temperature of 45 degree C. was maintained during coating. Atomisation pressure of 1.5 kg/cm$^2$ was maintained. A spray rate of 150 g hour was used. 810 g of moisture barrier coated carotenoid beadlets were obtained.

Example 7

Preparation of Beadlets Containing Lecithin

Lecithin (Epikuron 200, made by Degussa Bioactives, containing 95% phosphatidylcholine) 120 g, was dissolved in a mixture of 700 g ethanol and 800 g chloroform. A solution of 45 g of hydroxy propyl cellulose in 400 g isopropyl alcohol and 100 g methylene chloride was added to the above suspension along with 25 g cross-linked polyvinyl pyrrolidone. The suspension was strained through 100 mesh filter.

500 g of non-pareil seeds made of sugar, were charged in to a Uni-Glatt fluid bed processor with bottom spray, and warmed for 30 minutes at 35 degree C. The mixture suspension as prepared above was sprayed on the non-pareil seeds at the rate of 500 g/hour. The bed temperature was maintained at 35 degrees C. Atomisation pressure of 2.9 kg/cm$^2$ was maintained. 680 g of lecithin loaded beadlets were obtained.

60 g of polymer mixture comprising 10 g of ethyl cellulose and 70 g of hydroxypropyl methyl cellulose was dissolved in solvent mixture comprising 500 g of methylene chloride and 1000 g of isopropyl alcohol. 8 g of polyethylene glycol 600 was added as plasticiser. With this solution the coating was performed on carotenoid loaded non-pareil seeds in Uni-Glatt fluid bed coater using bottom spray technology at a spray rate of 400 g per hour. An atomization speed of 3 kg/cm$^2$ was maintained. Bed temperature of 45 degree C. was maintained through out the coating process. 740 g of oxygen-barrier coated beadlets were obtained.

120 g of sodium carboxymethyl cellulose dissolved in 300 g water, then mixed with 6 g of polyethylene glycol 400 and 2 g of titanium dioxide was sprayed on oxygen-barrier coated non-pareil seeds using Uni-Glatt fluid-bed coater using bottom spray mechanism. A bed temperature of 45 degree C. was maintained during coating. Atomisation pressure of 1.5 kg/cm$^2$ was maintained. A spray rate of 150 g/hour was used. 850 g of moisture barrier coated lecithin beadlets were obtained.

Example 8

Preparation of Beadlets Containing Natural Mixed Tocopherol in Vegetable Oil

Natural tocopherols in sunflower oil (Tocoblend L50) 80 g, was suspended in a mixture of 900 g isopropyl alcohol and 800 g chloroform. A solution of 80 g of polyvinyl pyrrolidone in 400 g isopropyl alcohol and 100 g methylene chloride was added to the above suspension along with 40 g ascorbyl palmitate and 12 g starch. The suspension was strained through 100 mesh filter.

400 g of non-pareil seeds made of sugar, were charged into a Uni-Glatt fluid bed processor with bottom spray, and warmed for 30 minutes at 35 degree C. The mixture as prepared above was sprayed on the non-pareil seeds at the rate of 500 g/hour. The bed temperature was maintained at 35 degree C. Atomisation pressure of 1.2 kg/cm$^2$ was maintained. 580 g of natural tocopherol loaded beadlets were obtained.

70 g of polymer mixture comprising 10 g of ethyl cellulose and 70 g of hydroxypropyl methyl cellulose was dissolved in solvent mixture comprising 500 g of methylene chloride and 1000 g of isopropyl alcohol. 8 g of polyethylene glycol 600 was added as plasticiser. With this solution the coating was performed on carotenoid loaded non-pareil seeds in Uni-Glatt fluid bed coater using bottom spray technology at a spray rate of 400 g per hour. An atomization speed of 1.2 kg/cm$^2$ was maintained. Bed temperature of 38 degree C. was maintained through out the coating process. 650 g of oxygen-barrier coated beadlets were obtained.

130 g of sodium carboxymethyl cellulose dissolved in 300 g water, then mixed with 6 g of Polyethylene glycol 400 and 2 g of titanium dioxide was sprayed on oxygen-barrier coated Non-pareil seeds using Uni-Glatt fluid-bed coater using bottom spray mechanism. A bed temperature of 45 degree C. was maintained during coating. Atomisation pressure of 1.5 kg/cm$^2$ was maintained. A spray rate of 150 g/hour was used. 650 g of moisture barrier coated mixed tocopherol beadlets were obtained.

Example 9

Preparation of Beadlets Containing Soy Bean Oil

Soya bean oil, 120 g, was suspended in a mixture of 400 g isopropyl alcohol and 800 g chloroform. A solution of 80 gm of polyvinyl pyrrolidone in 400 g isopropyl alcohol and 100 g methylene chloride was added to the above suspension along with 12 g of starch. The suspension was strained through 100 mesh filter.

400 g of non-pareil seeds made of sugar, were charged in to a Uni-Glatt fluid bed processor with bottom spray, and warmed for 30 minutes at 35 degree C. The mixture as prepared above was sprayed on the non-pareil seeds at the rate of 500 g/hour. The bed temperature was maintained at 35 degree C. Atomisation pressure of 1.2 kg/cm$^2$ was maintained. 590 g of soy oil loaded beadlets were obtained.

70 g of polymer mixture comprising 10 g of ethyl cellulose and 70 g of hydroxypropyl methyl cellulose was dissolved in solvent mixture comprising 500 g of methylene chloride and 1000 g isopropyl alcohol, 8 g of polyethylene glycol 600 was added as plasticiser. With this solution the coating was performed on oil-loaded non-pareil seeds in Uni-Glatt fluid bed coater using bottom spray technology at a spray rate of 400 g per hour. An atomization speed of 1.2 kg/cm$^2$ was maintained. Bed temperature of 38 degree C. was maintained through out the coating process. 650 g of oxygen-barrier coated beadlets were obtained.

130 g of sodium carboxymethyl cellulose dissolved in 300 g water, then mixed with 6 g of polyethylene glycol 400 and 2 g of titanium dioxide was sprayed on oxygen-barrier coated non-pareil seeds using Uni-Glatt fluid-bed coater using bottom spray mechanism. A bed temperature of 45 degree C. was maintained during coating. Atomisation pressure of 1.5 kg/cm$^2$ was maintained. A spray rate of 150 g/hour was used. 770 g of moisture barrier coated soy oil beadlets were obtained.

Preparation and Evaluation of Tablet Formulation of Beadlets

The beadlets of present invention (Examples 1-4) 32 g were mixed with dicalcium phosphate 40 g, microcrystalline cellulose 20 g, sodium starch glycolate 2 g, hydroxypropyl cellulose 3 g, aerosil 1 g and talcum 1 g. After uniform blending the powder mixture was compressed into tablets of 500 mg weight with hardness of 10 kg/cm$^2$.

TABLE 1

Properties of tablets compressed with beadlets of invention

| Beadlet sample no. | Angle of Repose | Tablet Disintegration time, in minutes | Friability, %. | Dissolution rate, % |
|---|---|---|---|---|
| Product of Example 1 | 23 degrees | 0.5 | 0.4 | 71.5 |
| Product of Example 2 | 25 degrees | 0.6 | 0.35 | 70.6 |
| Product of Example 3 | 24 degrees | 0.3 | 0.6 | 72.8 |
| Product of Example 4 | 24 degrees | 1.2 | 0.5 | 73 |
| Product of Example 5 | 25 degrees | 1.3 | 0.4 | 71.8 |

The flow property of the beadlets was assessed by determining the angle of repose under the method disclosed in Remington's Pharmaceutical Sciences, 16th Ed., page 1545. The current invention can include beadlets having an angle of repose between about 22 to about 27 degrees. Beadlets having an angle of repose between about 23 to about 25 degrees exhibit excellent flow properties. Accordingly, the beadlets can be formed to have an angle of repose between about 23 to about 25 degrees.

The tablets showed disintegration time, as determined by the procedure given in United States Pharmacopoeia USP23 page no. 1790, of less than 2 minutes and friability, as determined by procedure given in USP 23 page no 1981, of less than 1%. The dissolution rate was determined by procedure given in USP 23 page no. 1791. The tablets showed dissolution rate of more than 70%. When scored tablets were examined under scanning electron microscopy, the beadlets were found to be spherical and intact. The cross-section beadlets recovered from the tablet when examined under scanning electron microscopy revealed that the polymer coatings could withstand the compression force during tabletting and are in intact condition. No leaching of carotenoids into the tablet matrix was visible.

Stability Studies

The beadlet formulations of Example 1-4 were subjected to accelerated stability studies at 40 degree C. and 75% relative humidity. The beadlets were analyzed for carotenoid content before and after 6 months. The result of the study is shown in the following Table 2.

TABLE 2

Accelerated Stability of Beadlets at 40 Degree C. and at 75% Relative Humidity (RH)

| Beadlet sample | Initial analysis t-lutein | Final analysis t-lutein | Percent retention of t-lutein |
|---|---|---|---|
| Example 1 | 6.8% | 6.6% | 97.05% |
| Example 2 | 6.5% | 6.35% | 97.69% |
| Example 3 | 6.6% | 6.48% | 98.18% |
| Example 4 | 25.7% | 24.8% | 96.5% |
| Example 5 | 6.0% | 5.92% | 98.66% |

The above study concludes that the beadlets prepared by the present invention provide adequate stability to the carotenoid contained inside.

I claim:

1. Beadlets of lipophilic nutrients comprising an inert generally spherical core and a coating comprising stabilizing antioxidant, lipophilic nutrient, and a binding agent, the coating being applied on the inert generally spherical core as a colloidal suspension that is formed by a solution of the stabilizing antioxidant and the lipophilic nutrient that is first dispersed in a non-polar solvent, and then with addition of a polar solvent, and the colloidal suspension is mixed with the binding agent, the coating being applied by a bottom-spray fluidizing-bed system, the beadlets further comprising an oxygen barrier coating and a moisture barrier coating over the coating comprising the stabilizing antioxidant, lipophilic nutrient, and binding agent.

2. Beadlets as claimed in claim 1 wherein the lipophilic nutrient comprises a compound selected from the group consisting of lutein, lutein esters, alpha-carotene, beta-carotene, zeaxanthin, zeaxanthin esters, astaxanthin, lycopene, and mixtures thereof.

3. Beadlets as claimed in claim 1 wherein the lipophilic nutrient comprises xanthophyll esters containing lutein and zeaxanthin fatty acid esters in which about 90 wt. % to about 95 wt. % is trans-lutein esters, 0 wt. % to about 5 wt. % is cis-lutein esters and about 3.5 wt. % to about 6 wt. % is zeaxanthin esters.

4. Beadlets as claimed in claim 1 wherein the lipophilic nutrient comprises xanthophyll crystals comprising at least about 85 wt. % total xanthophylls in which at least about 90 wt. % is trans-lutein and/or zeaxanthin.

5. Beadlets as claimed in claim 1 wherein the lipophilic nutrient comprises a lipid selected from the group consisting of lecithin, mixed tocopherols or tocotrienols, plant stanols or phytosterols.

6. Beadlets as claimed in claim 1 wherein the beadlets comprise from about 1 wt. % to about 50 wt. % lipophilic nutrient.

7. Beadlets as claimed in claim 1 wherein the inert generally spherical core comprises a carbohydrate that does not react with the lipophilic nutrient, said carbohydrate is selected from the group consisting of sugar, mannitol, starch, sago, and microcrystalline cellulose.

8. Beadlets as claimed in claim 1 wherein the beadlets are in the form of spheres having a diameter between about 250 microns and about 3.5 mm.

9. Beadlets as claimed in claim 1 wherein the oxygen barrier coating comprising an oxygen barrier polymer selected from the group consisting of hydroxy propyl cellulose, hydroxy propyl methyl cellulose, methacrylate copolymers, polyvinyl pyrrolidone, ethyl cellulose, carboxymethyl cellulose, polyvinyl alcohol, and mixtures thereof.

10. Beadlets as claimed in claim 9 wherein the oxygen barrier coating further comprises a moisture barrier.

11. Beadlets as claimed in claim 9 wherein the beadlets comprise about 1 wt.% to about 40 wt. % oxygen barrier coating.

12. Beadlets as claimed in claim 1 wherein the moisture barrier coating comprising a moisture barrier polymer selected from the group consisting of carboxymethyl cellulose sodium, hydroxypropyl cellulose, hydroxypropylmethyl cellulose, methacrylate copolymers, polyvinyl alcohol, and mixtures thereof.

13. Beadlets as claimed in claim 12 wherein the beadlets comprise about 1 wt. % to about 40 wt. % moisture barrier coating.

14. Beadlets as claimed in claim 1 wherein the lipophilic nutrient is mixed, before coating, with a stabilising antioxidant wherein the stabilising antioxidant comprises an antioxidant selected from the group consisting of vitamin E acetate, natural tocopherols, ascorbyl palmitate, ascorbic acid, sodium ascorbate, citric acid, rosemary extract, rosemary oil, curcuminoids, green tea extract, ginger extract, carnosic acid, butylated hydroxy anisole, butylated hydroxy toluene, and combinations thereof.

15. Beadlets as claimed in claim 1 wherein the beadlets comprise about 0.1 wt. % to about 20 wt. % stabilising antioxidant.

16. Beadlets as claimed in claim 1 wherein the coating comprises disintegrating agents.

17. Beadlets as claimed in claim 1 wherein the beadlets comprise from about 0.1 wt. % to about 5 wt. % disintegrating agent, said disintegrating agent comprising a material selected from the group consisting of starch, cross-linked polyvinyl pyrrolidone, cross-carmellose sodium, sodium starch glycolate, and mixtures thereof.

18. Beadlets as claimed in claim 1, wherein the lipophilic nutrient is suspended in vegetable oil and said vegetable oil is selected from the group consisting of sunflower oil, safflower oil, corn oil, soya oil, peanut oil, partially or fully hydrogenated soya oil, vegetable oils having an unsaturated long chain fatty acid content of about 30 wt. % to about 90 wt. %, and mixtures thereof.

19. Beadlets as claimed in claim 1, wherein the inert generally spherical core comprises a generally spherical sugar core.

20. Beadlets as claimed in claim 1, wherein the lipophilic nutrient is a solubilized lipophilic nutrient in a mixture of at least one organic solvent.

21. Beadlets as claimed in claim 1, wherein the beadlets contain 25 to 50 wt % of lipophilic nutrient.

22. Beadlets as claimed in claim 1, wherein the non-polar solvent is methylene chloride, the polar solvent is isopropyl alcohol, and the binder is hydroxypropylmethyl cellulose.

23. Beadlets as claimed in claim 1, wherein a ratio of non-polar solvent to polar solvent ranges from about 0.2:1 to about 2:1.

24. Beadlets as claimed in claim 1, wherein the amount of binder ranges from about 0.1% to about 10% of the weight of the beadlets.

* * * * *